(12) United States Patent
Ahmad et al.

(10) Patent No.: US 11,291,640 B2
(45) Date of Patent: *Apr. 5, 2022

(54) ENDOXIFEN FOR THE TREATMENT OF BIPOLAR I DISORDER

(71) Applicant: Jina Pharmaceuticals, Inc., Libertyville, IL (US)

(72) Inventors: Ateeq Ahmad, Wadsworth, IL (US); Imran Ahmad, Libertyville, IL (US); Moghisuddin Ahmad, Wadsworth, IL (US); Shoukath M Ali, Vernon Hills, IL (US); Saifuddin Sheikh, Libertyville, IL (US)

(73) Assignee: Jina Pharmaceuticals, Inc., Libertyville, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/226,628

(22) Filed: Apr. 9, 2021

(65) Prior Publication Data

US 2021/0315843 A1    Oct. 14, 2021

Related U.S. Application Data

(60) Provisional application No. 63/008,141, filed on Apr. 10, 2020.

(51) Int. Cl.
| | |
|---|---|
| *A61K 31/138* | (2006.01) |
| *A61P 25/18* | (2006.01) |
| *A61P 25/24* | (2006.01) |
| *A61K 9/28* | (2006.01) |

(52) U.S. Cl.
CPC ............. *A61K 31/138* (2013.01); *A61K 9/28* (2013.01); *A61P 25/18* (2018.01); *A61P 25/24* (2018.01)

(58) Field of Classification Search
CPC ............................... A61K 31/138; A61P 25/18
See application file for complete search history.

(56) References Cited

U.S. PATENT DOCUMENTS

| 9,333,190 B2 | 5/2016 | Ahmad et al. |
| 10,376,479 B2 | 8/2019 | Ahmad et al. |
| 2012/0164075 A1 | 6/2012 | Ahmad et al. |

FOREIGN PATENT DOCUMENTS

| WO | 2009/120999 | 10/2009 |
| WO | 2012/050263 | 4/2012 |
| WO | 2014/141292 | 9/2014 |

OTHER PUBLICATIONS

Ahmad, et al., "Endoxifen, a New Treatment Option for Mania: A Double-Blind, Active-Controlled Trial Demonstrates the Antimanic Efficacy of Endoxifen", Clin Transl Sci (2016) 9, 252-259.
Ali, et al., "Endoxifen is a new potent inhibitor of PKC: A potential therapeutic agent for bipolar disorder", Bioorganic & Medicinal Chemistry Letters 20 (2010) 2665-2667.
Song, et al., "Suicidal Behavior During Lithium and Valproate Treatment: A Within-Individual 8-Year Prospective Study of 50,000 Patients With Bipolar Disorder", Am J Psychiatry 174:8, Aug. 2017, 795-802.
International Search Report and Written Opinion issued in International Application No. PCT/IB2021/052970, dated Jul. 13, 2021, 9 pages.

*Primary Examiner* — Theodore R. Howell
(74) *Attorney, Agent, or Firm* — Hamre, Schumann, Mueller & Larson, P.C.

(57) ABSTRACT

A method for maintaining a therapeutically effective concentration of endoxifen for the treatment of patient with bipolar I disorder is provided. The method includes administering to the patient a dose of 2 mg to 16 mg of endoxifen citrate in an enteric coated tablet once per day for at least 21 days. Further, the said method provides a desirable in-vivo plasma profile. The therapeutic dose monitoring is not required in a patient undergoing the said treatment. Furthermore, the method provides a significant improvement in mania assessed by the YMRS and the MADRS scores in patient undergoing the said treatment. Furthermore, the method as provides an early response time of the treatment in at least 2 days and remission time that is not more than 4 days in patient undergoing the said treatment.

6 Claims, No Drawings

ENDOXIFEN FOR THE TREATMENT OF BIPOLAR I DISORDER

FIELD OF THE INVENTION

The present disclosure relates to a method for maintaining a therapeutically effective concentration of endoxifen for the treatment of patient with bipolar I disorder, wherein the method comprises an administering to the patient, a dose of 2 mg to 16 mg of endoxifen citrate in an enteric coated tablet once per day for at least 21 days to patient in need thereof. Further, the said method provides a desirable an in-vivo plasma profile, and wherein therapeutic dose monitoring is not required in patient undergoing the said treatment. Furthermore, the said method provides a significant improvement in mania assessed by the YMRS and the MADRS scores in a patient undergoing the said treatment. Furthermore, the said method provides an early response time of the treatment in at least 2 days and remission time that is not more than 4 days in a patient undergoing the said treatment.

BACKGROUND OF THE INVENTION

Bipolar disorder is currently a major health problem. Bipolar disorder is a chronic, debilitating illness that affects up to 3% of the US population. It causes significant morbidity and imposes a burden on the society. The causes of bipolar disorder are still unknown, and no agent has been specifically developed on the basis of an understanding of the pathophysiology of the illness or mechanism of action for effective treatments.

Several drugs have been approved for treatment of bipolar disorder, such as lithium, valproate or divalproex sodium, carbamazepine, and atypical antipsychotics for the treatment of acute bipolar mania. While these drugs have provided relief for many individuals with bipolar disorder, significant issues with tolerability, efficacy, and attempt suicide or have suicidal behaviour still remain. Further, divalproex has a good tolerability but a high discontinuation rate. There is also a continuous need to observe the therapeutic dose monitoring in patients during the treatment. The clinicians, for example, may find themselves in situations in which better tolerated agents are less effective, and vice versa. Also, the adherence to the treatment is affected by adverse effects such as sedation, weight gain, alteration in thrombocytopenia, and thyroid disorders.

Study reported by Song et al. (2017) on around 51000 individuals with bipolar disorder, followed from 2005 to 2013 for treatment with lithium and valproate. Stratified cox regression was used to estimate the hazard ratios of suicide-related events during treated periods compared with untreated periods. For significant associations between medication and suicide-related events, the population attributable fraction was estimated to assess the public health impact for patients with bipolar disorder. During the follow-up, around more than 10000 suicide related events occurred. The incidence rate was significantly decreased by 14% during lithium treatment but not during valproate treatment. The difference in hazard ratios of suicide related events between lithium and valproate was statistically significant. Estimates of the population attributable fraction suggested that 12% of suicide related events could have been avoided if patients had taken lithium during the entire study.

Available treatments help a substantial proportion of patients, but are not beneficial for an estimated 40-50% of the population.

SUMMARY OF THE INVENTION

Protein kinase C (PKC) appears to have a role in bipolar disorder. PKC is involved in controlling the function of proteins through the phosphorylation of hydroxyl groups of serine and threonine amino acid residues on these proteins, which are known to play a vital role in cell signalling pathways. It regulates multiple neuronal processes implicated in mood regulation. In current clinical practice, mood stabilizers and antidepressants have been shown to modulate the PKC pathway. Disrupted PKC activity has been found both in post-mortem brains and platelet from patients with mood disorders. Accumulating evidence suggests an imbalance of the PKC signalling system in mood disorders. Thus, PKC is considered as a novel molecular target for the development of innovative medicine for bipolar disorder.

Targeting the PKC signalling pathway for bipolar disorder can improve the patient compliance, when therapeutic dose monitoring is not required in patient, and such treatment can provide significant improvement in mania and depression.

Endoxifen is a non-steroidal selective estrogen receptor modulator (SERM) of the triphenylethylene group. It is an active metabolite of tamoxifen and has been found to be effective in patients that have failed previous hormonal therapies (tamoxifen, aromatase inhibitors, and fulvestrant). The prodrug tamoxifen is metabolized by the CYP2D6 enzyme to produce afimoxifene (4-hydroxytamoxifen) and endoxifen. The chemical name of endoxifen citrate is (Z)-1-(4-Hydroxyphenyl)-1-{4-[2-(monomethylamino) ethoxy]phenyl}-2-pheny 1-1-butene citrate. The empirical formula of endoxifen citrate is $C_{25}H_{27}NO_2$—$C_6H_8O_7$, and has following chemical structure as given below (formula I):

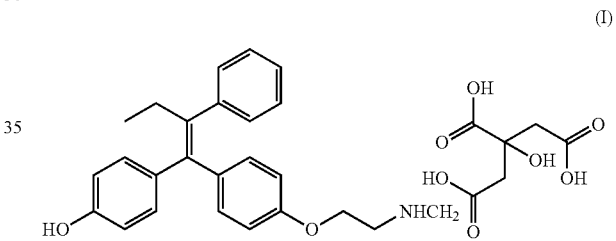

(I)

The exact mechanism by which endoxifen exerts its therapeutic effects have not been established in bipolar disorder. However, the efficacy of endoxifen could be mediated through PKC. The PKC represents a family of enzymes highly enriched in brain, where it plays a major role in regulating both pre- and post-synaptic aspects of neurotransmission. Excessive activation of PKC results in symptoms related to bipolar disorder. The PKC signalling pathway is clearly a target for the actions of two structurally dissimilar antimanic agents—lithium and valproate. Tamoxifen, a widely used breast cancer drug is also known to inhibit PKC and demonstrate antimanic properties in human. Endoxifen exhibited four-fold higher potency compared to tamoxifen in inhibiting the PKC activity and is not dependent on the isozyme cytochrome P450 2D6 (CYP2D6) for action on the target tissues. Endoxifen is a PKC inhibitor and is effective in the treatment of bipolar disorder. Further, endoxifen has a broad therapeutic index as compare to divalproex sodium.

An object of the present disclosure is to provide a method for maintaining a therapeutically effective concentration of endoxifen for treatment of bipolar I disorder in a patient.

Another object of the present disclosure is to provide a method for maintaining a therapeutically effective concentration of endoxifen for treatment of bipolar I disorder in a patient, wherein the patient has manic episodes with or without mixed features.

Another object of the present disclosure is to provide a method for maintaining a therapeutically effective concentration of endoxifen for treatment of bipolar I disorder in a patient, wherein the patient has depression or associated with depressive episodes.

Another object of the present disclosure is to provide a method for maintaining a therapeutically effective concentration of endoxifen for the treatment of patient with bipolar I disorder, wherein the method comprises administering to the patient, a dose of 2 mg to 16 mg of endoxifen citrate in an enteric coated tablet once per day.

Another object of the present disclosure is to provide a method for maintaining a therapeutically effective concentration of endoxifen for the treatment of patient with bipolar I disorder, wherein the method comprises administering to the patient, a dose of 2 mg to 16 mg of endoxifen citrate in an enteric coated tablet once per day for at least 21 days.

Another object of the present disclosure is to provide a method for maintaining a therapeutically effective concentration of endoxifen for the treatment of patient with bipolar I disorder, wherein the method comprises administering to the patient, a dose of 2 mg to 16 mg of endoxifen citrate in an enteric coated tablet once per day for at least 21 days and maintaining an in-vivo plasma profile in the patient including:
  a) a mean $C_{max}$ (ng/mL) of 10 to 180,
  b) a mean $AUC_{0-t}$ (ng.h/mL) of 50 to 3500, or
  c) a mean $T_{max}$ (h) of 6±2.

Another object of the present disclosure is to provide a method for maintaining a therapeutically effective concentration of endoxifen for the treatment of patient with bipolar I disorder, wherein the method comprises administering to the patient, a dose of 2 mg of endoxifen citrate in an enteric coated tablet once per day for at least 21 days and maintaining an in-vivo plasma profile in the patient including:
  a) a mean $C_{max}$ (ng/mL) of 10 to 25,
  b) a mean $AUC_{0-t}$ (ng.h/mL) of 50 to 500, or
  c) a mean $T_{max}$ (h) of 6±2.

Another object of the present disclosure is to provide a method for maintaining a therapeutically effective concentration of endoxifen for the treatment of patient with bipolar I disorder, wherein the method comprises administering to the patient, a dose of 4 mg of endoxifen citrate in an enteric coated tablet once per day for at least 21 days and maintaining an in-vivo plasma profile in the patient including:
  a) a mean $C_{max}$ (ng/mL) of 26 to 60,
  b) a mean $AUC_{0-t}$ (ng.h/mL) of 501 to 1000, or
  c) a mean $T_{max}$ (h) of 6±2.

Another object of the present disclosure is to provide a method for maintaining a therapeutically effective concentration of endoxifen for the treatment of patient with bipolar I disorder, wherein the method comprises administering to the patient, a dose of 8 mg of endoxifen citrate in an enteric coated tablet once per day for at least 21 days and maintaining an in-vivo plasma profile in the patient including:
  a) a mean $C_{max}$ (ng/mL) of 61 to 100,
  b) a mean $AUC_{0-t}$ (ng.h/mL) of 1001 to 2500, or
  c) a mean $T_{max}$ (h) of 6±2.

Another object of the present disclosure is to provide a method for maintaining a therapeutically effective concentration of endoxifen for the treatment of patient with bipolar I disorder, wherein the method comprises administering to the patient, a dose of 16 mg of endoxifen citrate in an enteric coated tablet once per day for at least 21 days and maintaining an in-vivo plasma profile in the patient including:
  a) a mean $C_{max}$ (ng/mL) of 101 to 180,
  b) a mean $AUC_{0-t}$ (ng.h/mL) of 2501 to 3500, or
  c) a mean $T_{max}$ (h) of 6±2.

Another object of the present disclosure is to provide a method for maintaining a therapeutically effective concentration of endoxifen for the treatment of patient with bipolar I disorder, wherein the method comprises administering to the patient, a dose of 2 mg to 16 mg of endoxifen citrate in an enteric coated tablet once per day for at least 21 days, wherein therapeutic dose monitoring is not required in patient undergoing the said treatment.

Another object of the present disclosure is to provide a method for maintaining a therapeutically effective concentration of endoxifen for the treatment of patient with bipolar I disorder, wherein the method comprises administering to the patient, a dose of 2 mg to 16 mg of endoxifen citrate in an enteric coated tablet once per day for at least 21 days, wherein the said method provides a significant improvement in mania assessed by the YMRS and the MADRS scores in patient undergoing the said treatment.

Another object of the present disclosure is to provide a method for maintaining a therapeutically effective concentration of endoxifen for the treatment of patient with bipolar I disorder, wherein the method comprises administering to the patient, a dose of 2 mg to 16 mg of endoxifen citrate in an enteric coated tablet once per day for at least 21 days to patient in need thereof, wherein the said method provides a significant improvement in mania assessed by the YMRS and MADRS score, wherein the YMRS score that is less than 25 and the MADRS score that is less than 3 after the treatment of 21 days.

Another object of the present disclosure is to provide a method for maintaining a therapeutically effective concentration of endoxifen for the treatment of patient with bipolar I disorder, wherein the method comprises administering to the patient, a dose of 2 mg to 16 mg of endoxifen citrate in an enteric coated tablet once per day for at least 21 days to patient in need thereof, wherein the said method provides an early response time of the treatment in at least 2 days and remission time that is not more than 4 days in patient undergoing the said treatment.

The objects described herein are directed to a method for maintaining a therapeutically effective concentration of endoxifen for the treatment of patient with bipolar I disorder, wherein the method comprises administering to the patient, a dose of 2 mg to 16 mg of endoxifen citrate in an enteric coated tablet once per day for at least 21 days to patient in need thereof. Further, the said method provides a desirable an in-vivo plasma profile, and wherein therapeutic dose monitoring is not required in patient undergoing the said treatment. Furthermore, the said method provides a significant improvement in mania assessed by the YMRS and the MADRS scores in patient undergoing the said treatment. Furthermore, the said method provides an early response time of the treatment in at least 2 days and remission time that is not more than 4 days in patient undergoing the said treatment.

DETAILED DESCRIPTION OF THE INVENTION

All terms as used herein in this application, unless otherwise stated, shall be understood in their ordinary meaning as known in the art. Other more specific definitions for certain terms as used in the present application are as set forth below and are intended to apply uniformly throughout the specification and claims unless an otherwise expressly set out definition provides a broader definition.

For the purposes of the present application, any ranges given include both the lower and the upper end points of the range. Ranges given should be considered approximate, unless specifically stated.

The term "YMRS" refers to Young Mania Rating Scale.
The term "MADRS" refers to Montgomery Asberg Depression Rating Scale.

The term "PP population" refers to per protocol population to those populations who completed the study without major protocol violations/deviations.

The term "mITT population" refers to modified Intent-To-Treat population to all randomized patients who received at least one dose of study medication and had data of at least one efficacy evaluation.

The term "EOT" refers to end of treatment.

The term "therapeutically effective concentration" refers to a concentration of endoxifen in plasma which is sufficient to decrease or prevent or cure the symptoms associated with a medical condition or infirmity or to normalize body functions in disease or disorders that result in impairment of specific bodily functions.

The term "response time" means an early indicator of treatment efficacy and it is not more than 2 days of treatment according to the embodiments described herein.

The term "remission time" refers to an absence or minimal symptoms of both mania and depression, which is not more than 4 days of treatment according to the embodiments described herein. Remission is the target of acute treatment.

The term "enteric coating" refers to any pharmaceutically acceptable coating preventing the release of the active agent in the stomach and sufficiently disintegrating in the intestine tract (by contact with approximately neutral or alkaline intestine juices) to allow the resorption of the active agent through the walls of the intestinal tract. The enteric coating remains intact in the acidic environment of the stomach and then solubilize in the more alkaline environment of the small intestine. Generally speaking, enteric coating helps in preventing gastric mucosal irritation and can be used for acid labile drugs which gets denatured in acidic medium.

In one embodiment the present application provides a method for maintaining a therapeutically effective concentration of endoxifen for treatment of bipolar I disorder in a patient.

In another embodiment the present application provides a method for maintaining a therapeutically effective concentration of endoxifen for treatment of bipolar I disorder in a patient, wherein the patient has manic episodes with or without mixed features.

In another embodiment the present application provides a method for maintaining a therapeutically effective concentration of endoxifen for treatment of bipolar I disorder in a patient, wherein the patient has depression or associated with depressive episodes.

In another embodiment the present application provides a method for maintaining a therapeutically effective concentration of endoxifen for the treatment of patient with bipolar I disorder, wherein the method comprises administering to the patient, a dose of 2 mg to 16 mg of endoxifen citrate in an enteric coated tablet once per day.

In another embodiment the present application provides a method for maintaining a therapeutically effective concentration of endoxifen for the treatment of patient with bipolar I disorder, wherein the method comprises administering to the patient, a dose of 2 mg to 16 mg of endoxifen citrate in an enteric coated tablet once per day for at least 21 days.

In another embodiment the present application provides a method for maintaining a therapeutically effective concentration of endoxifen for the treatment of patient with bipolar I disorder, wherein the method comprises administering to the patient, a dose of 2 mg to 16 mg of endoxifen citrate in an enteric coated tablet once per day for at least 21 days and maintaining an in-vivo plasma profile in the patient including:
  a) a mean $C_{max}$ (ng/mL) of 10 to 180,
  b) a mean $AUC_{0-t}$ (ng.h/mL) of 50 to 3500, or
  c) a mean $T_{max}$ (h) of 6±2.

In another embodiment the present application provides a method for maintaining a therapeutically effective concentration of endoxifen for the treatment of patient with bipolar I disorder, wherein the method comprises administering to the patient, a dose of 2 mg of endoxifen citrate in an enteric coated tablet once per day for at least 21 days and maintaining an in-vivo plasma profile in the patient including:
  a) a mean $C_{max}$ (ng/mL) of 10 to 25,
  b) a mean $AUC_{0-t}$ (ng.h/mL) of 50 to 500, or
  c) a mean $T_{max}$ (h) of 6±2.

In another embodiment the present application provides a method for maintaining a therapeutically effective concentration of endoxifen for the treatment of patient with bipolar I disorder, wherein the method comprises administering to the patient, a dose of 4 mg of endoxifen citrate in an enteric coated tablet once per day for at least 21 days and maintaining an in-vivo plasma profile in the patient including:
  a) a mean $C_{max}$ (ng/mL) of 26 to 60,
  b) a mean $AUC_{0-t}$ (ng.h/mL) of 501 to 1000, or
  c) a mean $T_{max}$ (h) of 6±2.

In another embodiment the present application provides a method for maintaining a therapeutically effective concentration of endoxifen for the treatment of patient with bipolar I disorder, wherein the method comprises administering to the patient, a dose of 8 mg of endoxifen citrate in an enteric coated tablet once per day for at least 21 days and maintaining an in-vivo plasma profile in the patient including:
  a) a mean $C_{max}$ (ng/mL) of 61 to 100,
  b) a mean $AUC_{0-t}$ (ng.h/mL) of 1001 to 2500, or
  c) a mean $T_{max}$ (h) of 6±2.

In another embodiment the present application provides a method for maintaining a therapeutically effective concentration of endoxifen for the treatment of patient with bipolar I disorder, wherein the method comprises administering to the patient, a dose of 16 mg of endoxifen citrate in an enteric coated tablet once per day for at least 21 days and maintaining an in-vivo plasma profile in the patient including:
  a) a mean $C_{max}$ (ng/mL) of 101 to 180,
  b) a mean $AUC_{0-t}$ (ng.h/mL) of 2501 to 3500, or
  c) a mean $T_{max}$ (h) of 6±2.

In another embodiment the present application provides a method for maintaining a therapeutically effective concentration of endoxifen for the treatment of patient with bipolar I disorder, wherein the method comprises administering to the patient, a dose of 2 mg to 16 mg of endoxifen citrate in an enteric coated tablet once per day for at least 21 days, wherein therapeutic dose monitoring is not required in patient undergoing the said treatment.

In another embodiment the present application provides a method for maintaining a therapeutically effective concentration of endoxifen for the treatment of patient with bipolar I disorder, wherein the method comprises administering to the patient, a dose of 2 mg to 16 mg of endoxifen citrate in an enteric coated tablet once per day for at least 21 days, wherein the said method provides a significant improvement in mania assessed by the YMRS and the MADRS scores in patient undergoing the said treatment.

In another embodiment the present application provides a method for maintaining a therapeutically effective concentration of endoxifen for the treatment of patient with bipolar I disorder, wherein the method comprises administering to the patient, a dose of 2 mg to 16 mg of endoxifen citrate in an enteric coated tablet once per day for at least 21 days to patient in need thereof, wherein the said method provides a significant improvement in mania assessed by the YMRS and MADRS score, wherein the YMRS score that is less than 25 and the MADRS score that is less than 3 after the treatment of 21 days.

In another embodiment the present application provides a method for maintaining a therapeutically effective concentration of endoxifen for the treatment of patient with bipolar I disorder, wherein the method comprises administering to the patient, a dose of 2 mg to 16 mg of endoxifen citrate in an enteric coated tablet once per day for at least 21 days to patient in need thereof, wherein the said method provides an early response time of the treatment in at least 2 days and remission time that is not more than 4 days in patient undergoing the said treatment.

The embodiments described herein are directed to a method for maintaining a therapeutically effective concentration of endoxifen for the treatment of patient with bipolar I disorder, wherein the method comprises administering to the patient, a dose of 2 mg to 16 mg of endoxifen citrate in an enteric coated tablet once per day for at least 21 days to patient in need thereof. Further, the said method provides a desirable an in-vivo plasma profile, and wherein therapeutic dose monitoring is not required in patient undergoing the said treatment. Furthermore, the said method provides a significant improvement in mania assessed by the YMRS and the MADRS scores in patient undergoing the said treatment. Furthermore, the said method provides an early response time of the treatment in at least 2 days and remission time that is not more than 4 days in patient undergoing the said treatment.

The present application has been described by way of example only, and it is to be recognized that modifications thereto falling within the scope, and spirit of appended claims, and which would be obvious to a person skilled in the art based upon the disclosure herein, are also considered to be within the scope of this disclosure.

Clinical Study Data:

Clinical study of an enteric coated tablet comprising endoxifen citrate formulation was carried out by administering to the patient doses of 2 mg to 16 mg of endoxifen citrate in an enteric coated tablet once per day for at least 21 days according to the present application.

Design of the Study:

The clinical study was a multicenter, randomized, double-blind, double-dummy, active controlled, parallel study to assess the efficacy and safety of endoxifen enteric coated tablet 8 mg and divalproex sodium extended release tablet 1000 mg in patients of bipolar I disorders.

Total 228 patients were enrolled in the study. All 228 patients were qualified for safety and mITT population and 213 patients were qualified for PP population.

The clinical trial study results are incorporated with different parameters as below,

TABLE 1

Descriptive statistics for total YMRS score at each visit (PP Population)

| Day | Statistics | T (N = 110) | R (N = 103) | p-value (between) |
|---|---|---|---|---|
| Day 0 (baseline) | n | 110 | 103 | 0.8229 |
| | Mean (SD) | 32.9 (8.52) | 33.1 (8.42) | |
| | Median | 31.0 | 33.0 | |
| | Min, Max | 20.0, 53.0 | 20.0, 55.0 | |
| Day 2 | n | 110 | 103 | 0.5070 |
| | Mean (SD) | 30.6 (9.53) | 31.3 (8.86) | |
| | Median | 28.5 | 29.0 | |
| | Min, Max | 13.0, 56.0 | 17.0, 55.0 | |
| | p-value (within) | <.0001 | <.0001 | |
| Day 4 | n | 110 | 103 | 0.8316 |
| | Mean (SD) | 28.6 (9.65) | 29.1 (9.13) | |
| | Median | 27.5 | 27.0 | |
| | Min, Max | 8.0, 56.0 | 15.0, 55.0 | |
| | p-value (within) | <.0001 | <.0001 | |

TABLE 1-continued

Descriptive statistics for total YMRS score at each visit (PP Population)

| Day | Statistics | T (N = 110) | R (N = 103) | p-value (between) |
|---|---|---|---|---|
| Day 7 | n | 110 | 103 | 0.9308 |
| | Mean (SD) | 25.7 (10.01) | 25.6 (9.48) | |
| | Median | 25.0 | 23.0 | |
| | Min, Max | 6.0, 53.0 | 5.0, 55.0 | |
| | p-value (within) | <.0001 | <.0001 | |
| Day 14 | n | 110 | 103 | 0.9034 |
| | Mean (SD) | 21.3 (9.54) | 21.5 (10.04) | |
| | Median | 20.0 | 20.0 | |
| | Min, Max | 2.0, 45.0 | 1.0, 58.0 | |
| | p-value (within) | <.0001 | <.0001 | |
| Day 21 (EOT) | n | 110 | 103 | 0.8858 |
| | Mean (SD) | 16.7 (9.80) | 16.7 (10.52) | |
| | Median | 16.0 | 16.0 | |
| | Min, Max | 0.0, 47.0 | 0.0, 58.0 | |
| | p-value (within) | <.0001 | <.0001 | |

Treatment Specification: T–> Test Product and R–> Reference Product.
Note 1:
p-value (between) is calculated using Wilcoxon-Rank Sum Test for comparison between Test and Reference treatments.
Note 2:
p-value (within) is calculated using Wilcoxon signed rank test for comparison of baseline to each visit for each treatment.

At day 21 (EOT), endoxifen yielded significant and sustained improvements in the YMRS score in patient with bipolar I disorders.

TABLE 2

Descriptive statistics for MADRS score at each visit (PP Population)

| Day | Statistics | T (N = 110) | R (N = 103) | p-value (between) |
|---|---|---|---|---|
| Day 0 (baseline) | N | 110 | 103 | 0.9857 |
| | Mean (SD) | 4.7 (3.32) | 4.6 (3.02) | |
| | Median | 4.0 | 4.0 | |
| | Min, Max | 0.0, 14.0 | 0.0, 12.0 | |
| Day 7 | N | 110 | 103 | 0.3815 |
| | Mean (SD) | 3.2 (2.93) | 2.7 (2.31) | |
| | Median | 3.0 | 2.0 | |
| | Min, Max | 0.0, 13.0 | 0.0, 9.0 | |
| | p-value (within) | <.0001 | <.0001 | |
| Day 14 | N | 110 | 103 | 0.6033 |
| | Mean (SD) | 2.6 (2.92) | 2.2 (1.96) | |
| | Median | 2.0 | 2.0 | |
| | Min, Max | 0.0, 18.0 | 0.0, 8.0 | |
| | p-value (within) | <.0001 | <.0001 | |
| Day 21 (EOT) | N | 110 | 103 | 0.4280 |
| | Mean (SD) | 2.3 (3.70) | 1.6 (2.06) | |
| | Median | 1.0 | 1.0 | |
| | Min, Max | 0.0, 22.0 | 0.0, 13.0 | |
| | p-value (within) | <.0001 | <.0001 | |

Treatment specification: T–> Test Product and R–> Reference Product.
Note 1:
p-value (between) is calculated using Wilcoxon-Rank Sum Test for comparison between Test and Reference treatments.
Note 2:
p-value (within) is calculated using Wilcoxon signed rank test for comparison of baseline to each visit for each treatments.

At day 21 (EOT), endoxifen yielded significant and sustained improvements in the MADRS score in patient with bipolar I disorders.

From the above table 1 and 2, it is evident that an early response time of the endoxifen treatment in at least 2 days and a remission time of endoxifen treatment is not more than 4 days in patient.

TABLE 3

Endoxifen pharmacokinetic data

| Simulated Data Variable | Pharmacokinetic Parameter Values | | | | |
|---|---|---|---|---|---|
| | 0.5 mg Endoxifen | 4 mg Endoxifen | 8 mg Endoxifen | 16 mg Endoxifen | 32 mg Endoxifen |
| $T_{max}$ (hr) | 5.9 ± 1.5 | 5.3 ± 1.5 | 5.3 ± 1.5 | 5.3 ± 1.5 | 5.3 ± 1.5 |
| $C_{min}$ (ng/mL) | 3.5 ± 0.5 | 27.4 ± 8.7 | 54.7 ± 17.3 | 109.4 ± 34.6 | 218.8 ± 69.2 |
| $C_{max}$ (ng/mL) | 4.8 ± 0.6 | 40.5 ± 12.1 | 80.9 ± 24.2 | 161.9 ± 48.4 | 323.9 ± 96.8 |
| $C_{avg}$ (ng/mL) | 4.2 ± 0.6 | 33.4 ± 10.9 | 66.7 ± 21.8 | 133.4 ± 43.7 | 266.8 ± 87.4 |
| $AUC_{0-t}$ (ng·h/mL) | 99.7 ± 13.7 | 800.3 ± 262.0 | 1600.6 ± 524.1 | 3201.3 ± 1048.1 | 6402.5 ± 2096.3 |
| Accumulation Index | 3.4 ± 1.0 | 3.8 ± 1.7 | 3.8 ± 1.7 | 3.8 ± 1.7 | 3.8 ± 1.7 | wherein, $T_{max}$ is the time at which the maximum plasma concentration occurs $C_{min}$ is the minimum plasma concentration $C_{max}$ is the maximum plasma concentration $C_{avg}$ is the average plasma concentration $AUC_{0-t}$ is the area under the plot of drug concentrations versus time curve, from time of drug administration (time "0") to time "t."

Therapeutic dose monitoring was not required during the clinical study because a steady state plasma concentration of endoxifen and its half-life was achieved throughout the treatment according to the embodiments described herein.

The invention claimed is:

1. A method for maintaining a therapeutically effective concentration of endoxifen for treatment of a patient with bipolar I disorder, said method comprising:
    administering to the patient a dose of 2 mg to 16 mg of endoxifen citrate in an enteric coated tablet once per day for at least 21 days,
    wherein the method does not comprise monitoring a therapeutic dose of the patient, and
    the patient has an early response time to the treatment in at least 2 days from starting the administration and a remission time that is not more than 4 days.

2. The method of claim 1, wherein the patient has manic episodes without mixed features.

3. The method of claim 1, wherein the patient has manic episodes with mixed features.

4. The method of claim 1, wherein the patient has depression.

5. The method of claim 1, wherein the patient has depressive episodes.

6. The method of claim 1, wherein the method maintains an in vivo plasma profile in the patient including:
    (a) a mean $C_{max}$ (ng/mL) of 10 to 180;
    (b) a mean $AUC_{0-t}$ (ng.h/mL) of 50 to 3500; and
    (c) a mean $T_{max}$ (h) of about 6±2.

* * * * *